United States Patent
Tanaka et al.

(10) Patent No.: US 7,056,310 B2
(45) Date of Patent: Jun. 6, 2006

(54) BODY FLUID MANAGEMENT DEVICE USED WITH ABSORBENT ARTICLE

(75) Inventors: Yuko Tanaka, Kobe (JP); Vincenzo D'Acchioli, Kobe (JP)

(73) Assignee: The Procter & Gamble Company, Cincinnati, OH (US)

(*) Notice: Subject to any disclaimer, the term of this patent is extended or adjusted under 35 U.S.C. 154(b) by 229 days.

(21) Appl. No.: 10/692,396

(22) Filed: Oct. 23, 2003

(65) Prior Publication Data

US 2004/0087919 A1    May 6, 2004

Related U.S. Application Data

(63) Continuation of application No. PCT/US01/13181, filed on Apr. 24, 2001.

(51) Int. Cl.
*A61M 1/00* (2006.01)
*A61F 5/44* (2006.01)
*A61F 13/15* (2006.01)

(52) U.S. Cl. ............ 604/327; 604/385.17; 604/385.19; 604/385.03; 604/355

(58) Field of Classification Search ............... 604/327, 604/385.17, 385.18, 385.14, 385.11, 385.19, 604/385.01, 393, 401, 385.03, 331, 355, 604/339

See application file for complete search history.

(56) References Cited

U.S. PATENT DOCUMENTS 5,304,161 A * 4/1994 Noel et al. ............... 604/378
6,229,061 B1 * 5/2001 Dragoo et al. ............ 604/358

FOREIGN PATENT DOCUMENTS

| JP | 2001-70341 | 3/2001 |
|----|-----------|--------|
| WO | WO 99/00084 | 1/1999 |
| WO | WO 99/00087 | 1/1999 |
| WO | WO 99/15123 | * 4/1999 |
| WO | WO 00/00114 | 1/2000 |
| WO | WO 00/00128 | 1/2000 |
| WO | WO/00/07637 | 2/2000 |
| WO | WO 00/40197 | 7/2000 |

* cited by examiner

*Primary Examiner*—Jacqueline F. Stephens
(74) *Attorney, Agent, or Firm*—George H. Leal; Jay A. Krebs; Ken K. Patel (57) ABSTRACT

A body fluid management device used with an absorbent article is disclosed. The body fluid management device has a body facing surface and an opposite surface facing the absorbent article when used with the absorbent article. The body fluid management device comprises a first attachment means provided on the body facing surface for attachment to the body of the wearer to cover the genitalia area of the wearer and an acquisition layer disposed between the body facing surface and the opposite surface. At least a portion of the body facing surface is fluid pervious and at least a portion of the opposite surface is fluid pervious such that fluid passes through the body fluid management device from the body facing surface toward the opposite surface.

11 Claims, 4 Drawing Sheets

BODY FLUID MANAGEMENT DEVICE USED WITH ABSORBENT ARTICLE

CROSS REFERENCE TO RELATED APPLICATION

This application is a continuation of International Application PCT/US01/13181, with an international filing date of Apr. 24, 2001.

TECHNICAL FIELD

The present application relates to a body fluid management device used with an absorbent article. More concretely, the present application relates to a body fluid management device to protect the genitalia area of the wearer of an absorbent article from body exudates discharged such as feces.

BACKGROUND

Body exudates management devices such as fecal management devices that are designed to be worn principally by incontinence persons and infants are known. Such fecal management devices are attached to the perianal region of the wearer and are intended to entrap and immediately contain fecal material and other bodily discharges. As a consequence, these devices are functionally effective in eliminating the problem of smearing on the skin of the wearer; in lessening epidermal irritation; in preventing contamination of articles such as clothing and bedding; and even in preventing the soiling of the carers themselves. Nevertheless, a problem often encountered during the use of such fecal management devices is that some of the fecal material can flow towards the sensitive genitalia area of the wearer in particular for female wearers into the vestibule of the wearer. Typically, the presence of such fecal material can lead to a nasty infections in this area. Such a condition is most undesirable, painful and distressing to the bedridden wearer or to the infant.

Many attempts have been made to prevent fecal material from leaking out of the fecal management device. One attempt for improvement is to provide a means to closely contact the fecal management device to the wearer's skin. Such a fecal management device has a bag to contain fecal material therein. The bag has an opening to receive fecal material therethrough. The bag also has an adhesive attachment means at the periphery of the opening such that the opening of the bag is secured to the perianal area of the wearer to achieve improved fit between the wearer's skin and the fecal management device.

Another improvement for leakage prevention of fecal material is disclosed in, e.g., PCT Publication No. WO 99/00084 published on Jan. 7, 1999. WO 99/00084 discloses a fecal management device comprising a bag having an aperture and an anatomically-shaped flange which surrounds the aperture. The flange provides for adhesive attachment to the perianal area of the wearer. In particular, the front portion of the flange comprises a projection which provides an effective seal between the flange and the skin of the wearer and prevent leakage to the genitalia area. The device fits snugly into the folds at the margin of the genitalia area of the wearer and thereby improves sealing. PCT Publication No. WO 00/00128 published on Jun. 6, 2000 discloses a fecal management device having a bag and a flange. The flange comprises a projection in the rear portion of the flange to provide an effective seal between the flange and skin of the wearer at the rear. PCT Publication No. WO 99/00087 published on Jan. 7, 1999 discloses a fecal management device having a bag and a flange. The flange comprises a projection in the front portion and the rear portion of the flange, respectively which provides an effective seal between the flange and skin of the wearer at the front and rear.

These attempts are effective in forming improved fit between a fecal management device and the skin of the wearer to prevent leakage of fecal material through a gap between the device and the skin toward the genitalia area of the wearer. However, fecal material contained in the bag could explosively leak from the bag by, e.g., body pressure to compress the bag and the fecal material contained in the bag. If this happens, the genitalia area of the wearer is contaminated by the fecal material leaked from the bag. Thus, it is desirable to provide a device to cover the genitalia area of the wearer to protect the genitalia area from body discharges such as fecal material.

SUMMARY

The present invention is relevant to a body fluid management device used with an absorbent article. The body fluid management device has a body facing surface and an opposite surface facing the absorbent article when used with the absorbent article. The body fluid management device comprises a first attachment means provided on the body facing surface for attachment to the body of the wearer to cover the genitalia area of the wearer and an acquisition layer disposed between the body facing surface and the opposite surface. At least a portion of the body facing surface is fluid pervious and at least a portion of the opposite surface is fluid pervious such that fluid passes through the body fluid management device from the body facing surface toward the opposite surface.

The present invention is further relevant to a body exudates management device used with an absorbent article. The body exudates management device comprises a body fluid management device and a bag. The body fluid management device has a body facing surface and an opposite surface facing the absorbent article when used with the absorbent article and comprises a first attachment means provided on the body facing surface for attachment to the body of the wearer to cover the genitalia area of the wearer and an acquisition layer disposed between the body facing surface and the opposite surface. At least a portion of the body facing surface is fluid pervious and at least a portion of the opposite surface is fluid pervious such that fluid passes through the body fluid management device from the body facing surface toward the opposite surface. The bag has a bag aperture and a second attachment means for attachment to the perianal area of the wearer, the second attachment means provided adjacent to the bag aperture. The body fluid management device is joined to the bag.

These and other features, aspects, and advantages of the invention will become evident to those skilled in the art from a reading of the present disclosure.

BRIEF DESCRIPTION OF THE DRAWINGS

While the specification concludes with claims particularly pointing out and distinctly claiming the invention, it is believed that the present invention will be better understood from the following description of preferred embodiments taken in conjunction with the accompanying drawings in which:

DETAILED DESCRIPTION

All references cited herein are incorporated herein by reference in their entireties. Citation of any reference is not an admission regarding any determination as to its availability as prior art to the claimed invention.

As used herein, the term "comprising" means that other steps and other ingredients which do not affect the end result can be added. This term encompasses the terms "consisting of" and "consisting essentially of."

As used herein, the term "genitalia" or "genitalia area" refers to external genitalia. The external genitalia includes the portion of the wearer body including labia majora, labia minora, clitoris, vestibule, urethra, and vagina for female, and the portion of the wearer body including penis for male. As used herein, "body exudates management device" refers to devices which covers at least the perianal area of the wearer to collect and contain feces into the device. A body exudates management device includes a body fluid management device. A body exudates management device also includes a fecal management device. As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). As used herein, the term "diaper" refers to an absorbent article generally worn by infants and incontinent persons that is worn about the lower torso of the wearer.

Figure 1:
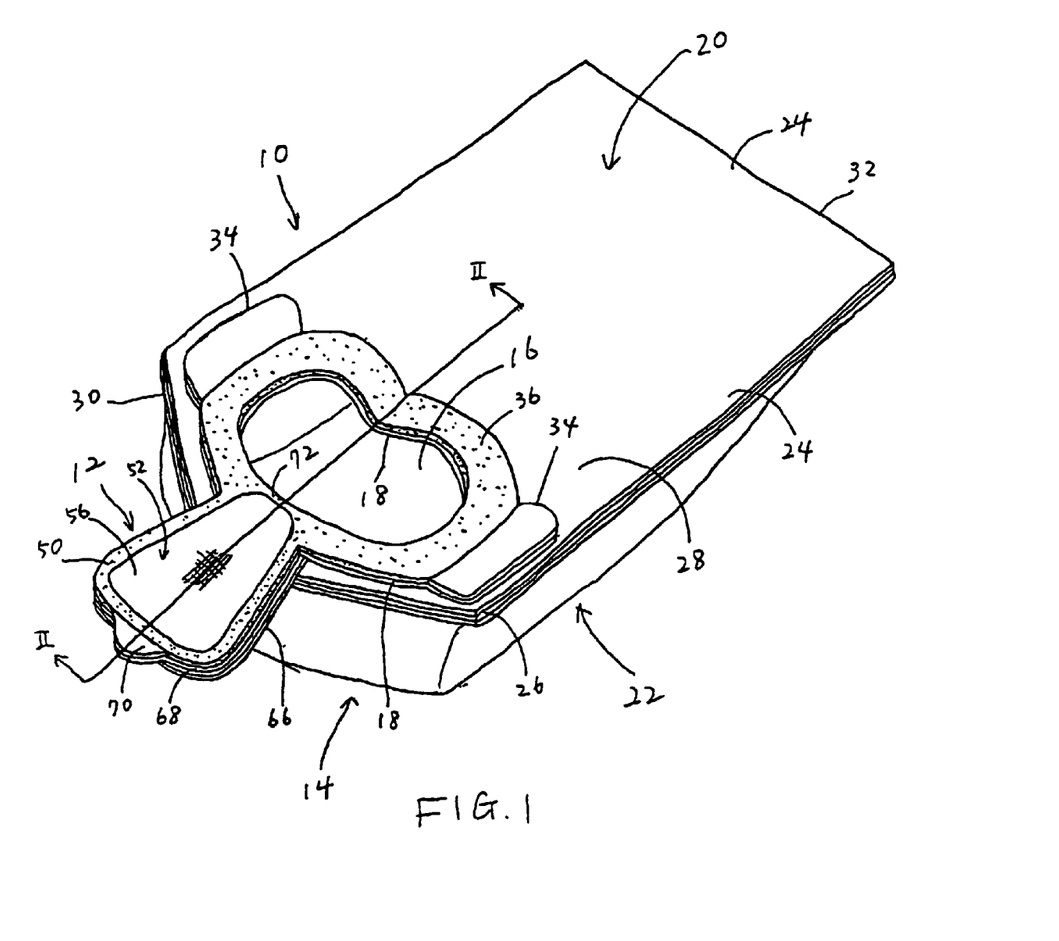
FIG. 1 is a perspective view of a body exudates management device comprising a body fluid management device and a bag as one embodiment of the present invention.

FIG. 1 is a perspective view of the body exudates management device 10 having the body fluid management device 12 as one embodiment of the present invention. More concretely, the body exudates management device 10 has a bag 14 and the body fluid management device 12 joined to the bag 14. As used herein, the term "joined" or "joining" encompasses configurations whereby an element is directly secured to the other element by affixing the element directly to another element, and configurations whereby the element is indirectly secured to the other element by affixing the element to intermediate member(s) which in turn are affixed to the other element. The body exudates management device 10 is used with an absorbent article such as a disposable diaper. The body exudates management device 10 may be put inside the disposable diaper when in use.

The body fluid management device 12 is intended to be used adjacent to the genitalia area of the wearer, preferably to cover the genitalia of the wearer to protect the genitalia area from body exudates such as fecal material. The body fluid management device prevents the genitalia area of the wearer from being exposed to fecal material which may be flowing in the absorbent article or at least reduces such an exposure of the genitalia area to the fecal material, whereby preventing or at least reducing contamination of the genitalia area by fecal material. The body fluid management device covers the genitalia area of the male wearer or the female wearer. The body fluid management device is especially useful when used for female to maintain the complex anatomy of the female genitalia clean and eliminating nasty infections by fecal material in the female genitalia. Because the body fluid management device is intended to be positioned to cover the genitalia area including the urethra and/or vagina of the wearer, the body fluid management device should have fluid permeability for urine and/or menses from the body side of the device to the opposite side of the device. Preferably, the body fluid management device is also able to acquire body fluids quickly such that the body fluid management device quickly removes body fluids such as urine or menses from the body or from the space between the body and the body fluid management device. Preferably, the body fluid management device 12 does not retain body fluid therein or drain most of body fluid out of the body fluid management device 12.

Figure 2:
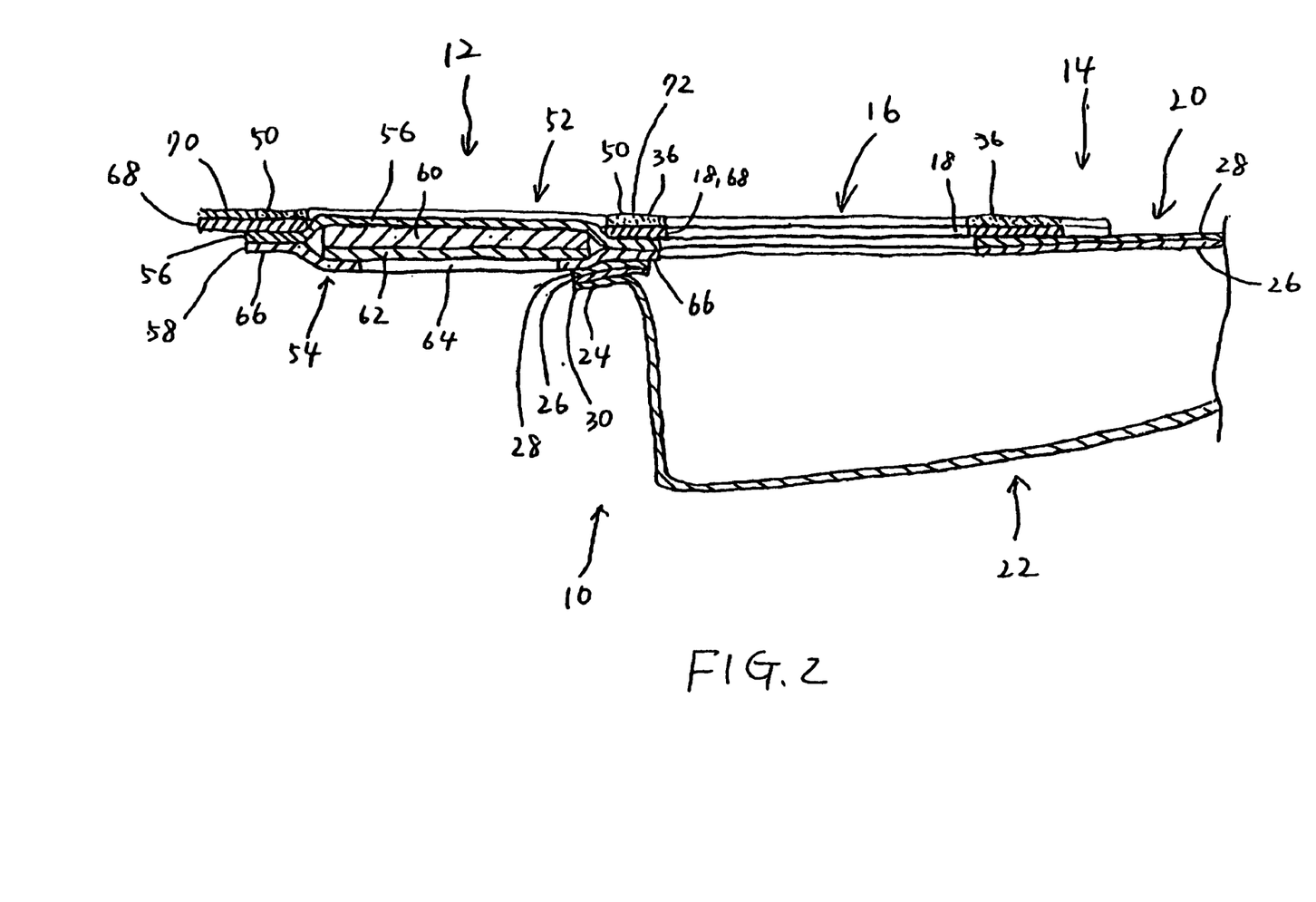
FIG. 2 is a cross-sectional view of FIG. 1 taken along the line II—II.
Figure 3:
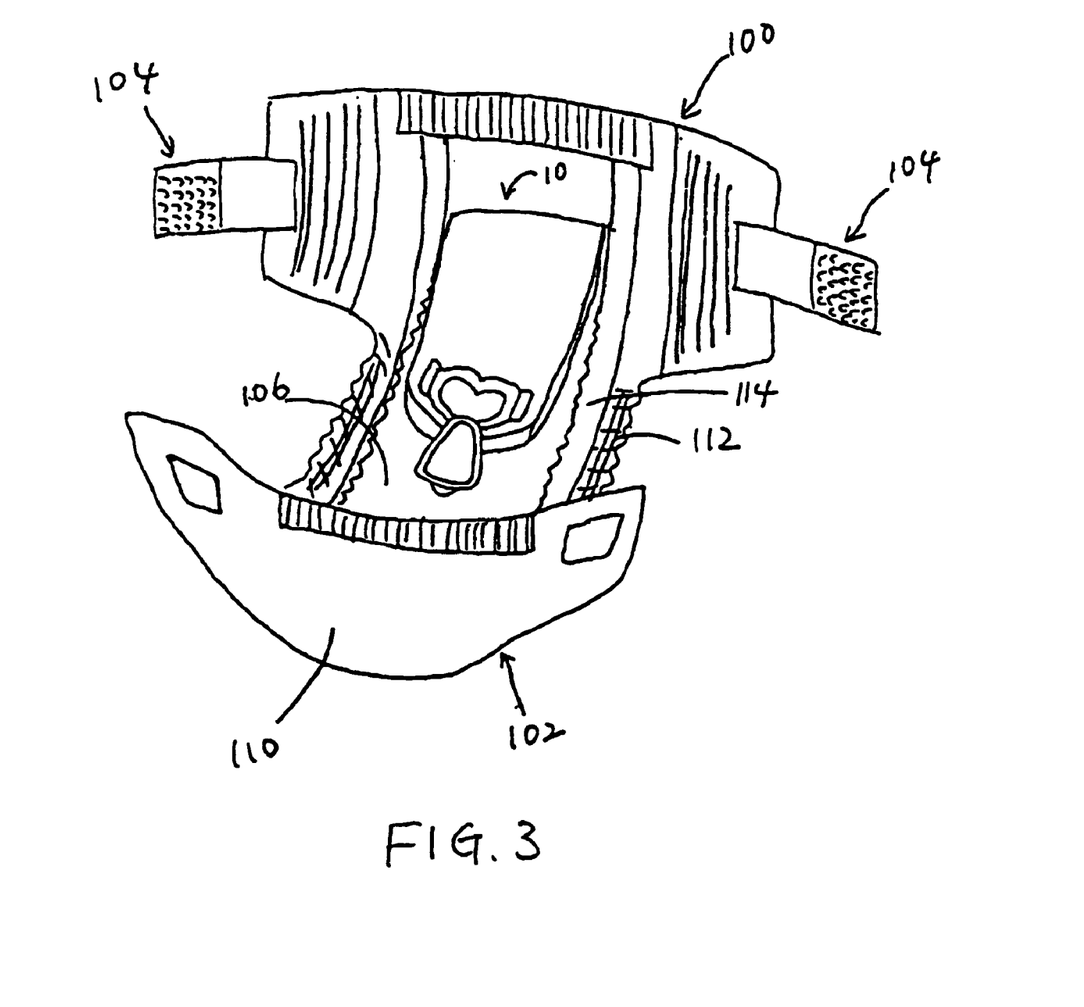
FIG. 3 is a perspective view of one embodiment of the body exudates management device used with a disposable diaper as an example for an absorbent article.

The body fluid management device 12 may be any shape or size. The body fluid management device 12, when used for female, preferably has a size to cover and protect the genitalia area, preferably may have a size to cover a portion of perineum of the wearer as well as the genitalia area. However, the body fluid management device should not cover anus. The body fluid management device may be flat or preferably may be anatomically shaped such that the device follows the contours of the body to which the body fluid management device attached. The body fluid management device 12 shown in FIGS. 1–3 is one embodiment of a body fluid management device designed for female. Alternatively, the body fluid management device, when used for male, preferably has a size to cover and protect the penis of the wearer, preferably may have a size to cover a portion of or the entirety of scrotum as well as the penis. The body fluid management device for male may be flat, cup-shaped, or preferably may be anatomically shaped such that the device follows the contours of the body to which the body fluid management device attached. A cup-shaped device is preferable for male.

The body fluid management device 12 has a body facing surface 52 and an opposite surface 54 facing an absorbent article when used with the absorbent article. The body fluid management device 12 comprises a first attachment means 50 provided on the body facing surface 52 of the body fluid management device 12 for attachment to the body of the wearer to cover the genitalia area. The body fluid management device 12 also comprises an acquisition layer 60 (shown in FIG. 2) disposed between the body facing surface 52 and the opposite surface 54. At least a portion of the body facing surface 52 is fluid pervious and at least a portion of the opposite surface 54 is fluid pervious such that fluid passes thorough the body facing surface 52 and the opposite surface 54. The entirety of the body facing surface 52 may be fluid pervious. The entirety of the opposite surface 54 may be fluid pervious.

In the embodiment shown in FIGS. 1 and 2, the body fluid management device 12 shown in FIGS. 1 and 2 has a flat pad-like configuration. The body fluid management device 12 of the embodiment preferably comprises a fluid pervious topsheet 56 disposed on the body facing surface 52, a fluid pervious backsheet 58 disposed on the opposite surface 54, an acquisition layer 60 disposed underneath the topsheet 56, and a distribution layer 62 disposed underneath the acquisition layer 60. Another acquisition layer may be provided underneath the distribution layer 62. However, the body fluid management device 12 does not have to have all of these elements as far as the body fluid management device 12 has fluid permeability and protects the genitalia area of the wearer. Alternatively, any other layer or material may be inserted into any place of the structure of the body fluid management device 12, e.g., to enhance functions of the body fluid management device 12 such as fluid permeability from the body facing surface 52 to the opposite surface 54, quick acquisition of body fluid, and/or quick drainage of body fluid out of the body fluid management device 12. The body fluid management device 12 also comprises a first attachment means 50 provided on the body facing surface 52 of the body fluid management device 12 for attachment to the body of the wearer to cover the genitalia area of the wearer.

The fluid pervious topsheet 56 is disposed on the body facing surface 52 and is preferably joined to the fluid pervious backsheet 58 preferably along the periphery of the topsheet 56 and the backsheet 58 by attachment means (not shown) such as adhesive, heat, pressure, or heat and pressure to form a peripheral edge 66.

The fluid pervious topsheet 56 is preferably compliant, soft feeling, and non-irritating to the wearer's skin. Further, the topsheet 56 is fluid pervious permitting body fluids (e.g., urine or menses) to readily penetrate through its thickness. A suitable topsheet 56 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. The topsheet 56 is preferably made of a hydrophobic material to isolate the wearer's skin from body fluids which have passed through the topsheet 56 and to prevent rewet. If the topsheet 56 is made of a hydrophobic material, at least the upper surface of the topsheet 56 may be treated to be hydrophilic so that body fluids will transfer through the topsheet more rapidly. This diminishes the likelihood that body fluids will flow off the topsheet 56 rather than being drawn through the topsheet 56 and being acquired by the acquisition layer 60. The topsheet 56 can be rendered hydrophilic by treating it with a surfactant. Suitable methods for treating the topsheet 56 with a surfactant include spraying the topsheet 56 material with the surfactant and immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al on Jan. 29, 1991 and U.S. Pat. No. 4,988,345 entitled "Absorbent Articles with Rapid Acquiring Absorbent Cores" issued to Reising on Jan. 29, 1991, each of which is incorporated by reference herein.

An alternative preferred topsheet comprises an apertured formed film. Apertured formed films are preferred for the topsheet because they are pervious to body fluids and yet non-absorbent and have a reduced tendency to allow body fluids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel. et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr et al. on Jul. 31, 1984; and U.S. Pat. No. 5,006,394 "Multilayer Polymeric Film" issued to Baird on Apr. 9, 1991. Each of these patents are incorporated herein by reference.

The fluid pervious backsheet 58 is disposed on the opposite surface 54 and is preferably joined to the fluid pervious topsheet 56. The fluid pervious backsheet 58 is fluid pervious permitting body fluids (e.g., urine or menses) to readily pass through its thickness from the body side toward the absorbent article side when used with the absorbent article. The fluid pervious backsheet 58 may comprise any of the materials which is suitable for the use of the fluid pervious backsheet 56 as described above. The fluid pervious backsheet 58 may have fluid permeability more than the fluid pervious topsheet 56 to allow quick fluid transfer from the body fluid management device 12 to an absorbent article. In the embodiment shown in FIG. 2, the fluid pervious backsheet 58 comprises a fluid impervious material such as a plastic film comprising, e.g., polyethylene and/or polypropylene. The fluid impervious material may be the material to permit vapors to escape therethrough. In order to provide fluid permeability to the fluid impervious material in the embodiment shown in FIG. 2, a backsheet aperture 64 is formed in the backsheet 56. The backsheet aperture 64 may comprise one opening which is the almost same size as the acquisition layer 60 or the distribution layer 62 if provided but a little smaller than that to support the periphery of the acquisition layer 60 or the distribution layer 62. Alternatively, the backsheet aperture 64 may comprise a plurality of openings formed in the backsheet 56. The aperture size is selected preferably so as not to interfere with fluid passage through the backsheet aperture 64. The total opening area of the backsheet aperture 64 may be not less than 20 $cm^2$, preferably 50 cm2, more preferably 100 cm2. It should be noted, however, that the range herein is to depict a desirable range and may be smaller than the range described herein as far as it is sufficient for smooth fluid penetration. The upper limit of the average opening size is arbitrarily. It is typically determined by the constraint of the design of the device (e.g., the average aperture size can not exceed the size of the device).

The acquisition layer 60 is disposed underneath the fluid pervious topsheet 56 so as to be capable of rapidly acquiring a majority of body fluid away from the topsheet 56 and preferably to be capable of transferring a majority of body fluid toward the underlying layer such as a distribution layer 62 if provided or toward a topsheet of an absorbent article. The acquisition layer 60 may be manufactured from a wide range of materials such as porous foams, reticulated foams, apertured plastic films, or woven or nonwoven webs of natural fibers (eg. wood or cotton fibers), synthetic fibers (eg. polyester or polypropilene fibers) or a combination of natural and synthetic fibers. If the acquisition layer includes fibers, the fibers may be spunbond, carded, wet-laid, melt-blown, hydroentangled, or otherwise processed as is known in the art. The acquisition layer 60 is designed to have a pore size such that the material of the underlying layer such as a distribution layer 62 or a topsheet of the absorbent article is not allowed to pass through and contact the wearer's skin. While not to have large of a pore size which permits the passage of the underlying layer, the acquisition layer 60 preferably has a pore size which is greater than pore size of the underlying layer. Preferably the acquisition layer 60 is less hydrophilic than the underlying layer. The acquisition layer 60 may be treated with a surfactant to increase its initial wettability. When treated with surfactant however the acquisition layer 60 should still be less hydrophilic than the underlying layer. Suitable methods for treating the acquisition layer with a surfactant include spraying the acquisition layer 60 with the surfactant and immersing the material into the surfactant. Alternatively, a surfactant may be incorporated into the acquisition layer.

The distribution layer 62 may be provided underneath the acquisition layer 60 to absorb body fluid (such as urine or menses) from the acquisition layer 60 to prevent body fluid from returning to the body of the wearer from the acquisition layer 60 or at least reduce the return of body fluid. The distribution layer 62 is preferably able to transfer a majority of the body fluid to the underlying layer such as a topsheet of an absorbent article. Another acquisition layer may be provided underneath the distribution layer 62 to further transfer body fluid away from the body of the wearer. It is desirable that the distribution layer materials exhibit a certain hydrophilicity. However, this does not necessarily mean that these have to be completely hydrophilic (i.e., have a wetting angle for water of approximately zero), nor that this hydrophilicity has to be uniformly across all surfaces in all regions. Hydrophilicity can be achieved by starting from hydrophilic base materials, such when using cellulosic fibers, or polymeric material which mostly are relatively hydrophobic with resin incorporated or surface applied surfactants. Alternatively, the distribution material itself can further be hydrophilicised as such, e.g., after forming a web comprising hydrophobic materials, this can be rendered hydrophilic by addition of surfactants.

Many porous materials are contemplated to be suitable for materials for the distribution layer 62. Particularly preferred materials are fibrous wet-laid webs comprising wide variety of resilient fibers. Apart from well know synthetic fibers such as being based on polyethyleneterephatalate, polyester, polyamine, resilient polyolefins or combinations thereof, e.g., in bi-component fiber form, a particularly preferred fiber is a chemically-stiffened, twisted bulking cellulosic fiber.

As used herein, the term "chemically stiffened, twisted, and curled fibers" means any fibers which have been stiffened by a chemical means to increase stiffness of the fibers under both dry and aqueous conditions. Such a means includes the addition of chemical stiffening agents which, for example, coat and/or impregnate the fibers. Such a means also includes the stiffening of the fibers by altering the chemical structure of the fibers themselves, e.g., by cross-linking polymer chains. Without wishing to be bound by theory, in addition to being hydrophilic, these stiffened fibers are preferably substantially "hornified". Thus, the cell walls do not swell appreciably and maintain the void volume within the network when wetted. Chemically stiffened, twisted, and curled cellulosic fibers provide permeability, flexibility, and increased hydrophilicity. For exemplary purposes, other polymeric stiffening agents which can coat or impregnate cellulosic fibers include: cationic modified starch having nitrogen-containing groups (e.g., amino groups) latex; wet strength resins such as polyamide-epichlorohydrin resin, example crosslinking agents can be applied to the fibers which, subsequent to application, are caused to chemically form intra-fiber crosslink bonds. These crosslink bonds can increase stiffness of the fibers. Whereas the utilization of intrafiber crosslink bonds to chemically stiffen the fibers is preferred, it is not meant to exclude other types of reactions for chemical stiffening of the fibers. In the more preferred stiffened fibers, chemical processing includes intrafiber crosslinking with crosslinking agents while such fibers are in a relatively dehydrated, defibrillated (i.e., individualised), twisted, curled condition. Suitable chemical stiffening agents include monomeric crosslinking agents including, but not limited to, C2–C8 dialdehydes and C2–C8 monoaldehydes having an acid functionality to form the crosslinking solution. These compounds are capable of reacting with at least two hydroxyl groups in a single cellulose chain or on approximately located cellulose chains in a single fiber. Such crosslinking agents contemplated for use in preparing the stiffened cellulose fibers include, but are not limited to, glutaraldehyde, glyoxal, formaldehyde, and glyoxylic acid. Other suitable stiffening agents are polycarboxylates, such as citric acid. The effect of crosslinking under these conditions is to form fibers which are stiffened and which tend to retain their twisted, curled configuration during use in the absorbent articles herein.

The first attachment means 50 is provided on the body facing surface 52 of the body fluid management device 12 for attachment to the body of the wearer to cover the genitalia area of the wearer. Preferably, the first attachment means 50 is provided on the periphery edge 66 of the body fluid management device 12 such that the first attachment means 50 does not interfere with body fluid passing through the fluid pervious topsheet 56. However, minimal amount of attachment means may be provided on a portion of the fluid pervious topsheet 56 inboard of the peripheral edge 66 for secure attachment. The first attachment means 50 is provided preferably along the entirety of the peripheral edge 66 to prevent body exudates such as fecal material from entering into the space between the wearer's body and the body facing surface 52 of the body fluid management device 12 through a gap between the device and the body along the peripheral edge 66. Alternatively, the first attachment means may be provided along a portion of the peripheral edge 66 such that a portion of the peripheral edge 66 does not have the first attachment means. This allows air circulation into the space between the body facing surface 52 and the skin of the wearer. The first attachment means 50 may be provided directly on the peripheral edge 66 formed by the periphery of the topsheet 56 and the periphery of the backsheet 58. Alternatively, the first attachment means 50 may be provided on the peripheral edge 66 through a flange (such as a flange sheet) which is joined to the peripheral edge 66 (e.g., in the embodiment shown in FIGS. 1 and 2, the first attachment means 50 is joined to the first flange sheet 68, and then the first flange sheet 68 is joined to the peripheral edge 66).

The first attachment means 50 may be any material which is safely used for attachment of the body fluid management device 12 to the body of the wearer. Such attachment means include straps and more preferably comprises a body-compatible pressure sensitive adhesive. Any medically approved water resistant pressure sensitive adhesive may be used for the attachment means 50, such as hydrocolloid adhesives, hydrogel adhesives or oil based adhesives. Particularly effective adhesives in providing the desired adhesive properties to secure to the skin of the wearer at the sensitive genitalia area, whilst allowing for relatively painless application and removal, are formed from crosslinking polymers with a plastisicer to form a 3-dimensional matrix. The first attachment means 50 can be applied to the peripheral edge 66 or the first flange sheet 68 if provided by any means known in the art such as slot coating, spiral, or bead application or printing. The attachment means 50 may be applied at a basis weight of from 20 g/m² to 2500 g/m², preferably from 500 g/m² to 2000 g/m², more preferably from 700 g/m² to 1500 g/m² depending on the end use envisioned. For example for the genital protection device 12 to be used for babies the amount of the attachment means 50 may be less than for body exudates management devices designed for active adult incontinence sufferers. The first attachment means 50 is preferably covered with a release means (not shown) in order to protect the first attachment means 50 such as siliconized paper. Before application of the body exudates management device 10 to the skin of the wearer, the release means if present is removed.

The first flange sheet 68, if provided (in the embodiment shown in FIGS. 1 and 2, it is provided), is joined to the peripheral edge 66 according to any means known to the skilled in the art which may provide permanent or releasable attachment. Preferably, the first flange sheet 68 is attached to the peripheral edge 66 by adhesive. The first flange sheet 68 may be provided in any size depending on the wearer group for which the device is intended. Similarly the first flange sheet 68 may be provided in any shape. In the embodiment shown in FIGS. 1 and 2, the first flange sheet 68 is generally coextensive with the first attachment means 50, more preferably is a little larger than the first attachment means 50 to support the entirety of the first attachment means 50. The first flange sheet 68 may have a lobe 70 which is non-adhesive and can thereby serve to facilitate placement and removal of the device whilst avoiding contact with the adhesive. The lobe 70 may be provided with a soft material such as a nonwoven thereon. In the embodiment shown in FIG. 1, the first flange sheet 68 is substantially flat, but may be anatomically shaped.

The first flange sheet 68 is preferably made of soft, flexible and malleable material to allow easy placement of the flange to the perianal area. Exemplary materials include nonwoven materials, wovens, open celled thermoplastic foams, closed-cell thermoplastic foams, composites of open celled foams and stretch nonwoven, and films. A closed-cell foam of polyethylene has been found effective, but more preferably an open celled polyurethane foam is used. Preferably, such foams have a thickness within the general range of 0.1 to 5 millimetres and a density of 5 to 250 g/m², more preferably 50 g/m². Other thermoplastic foam materials, or other suitable plastics sheet materials having the described properties of such foams (i.e., softness, pliability, stretchability, and contractability) might also be used.

The bag 14 of the body exudates management device 10 has a bag aperture 16 and a second attachment means 36 for attachment to the perianal area of the wearer. The second attachment means 36 is provided adjacent to the bag aperture 16.

The bag 14 as used herein is a receptacle for the containment of excreted fecal material. The bag 14 can be provided in any shape or size depending on the intended use thereof, i.e. whether the device is intended for bedridden patients or active patients suffering from incontinence or requiring an artificial bowel or for infants. For example elongated bags which are principally tubular or rectangular are typically utilized by bedridden patients and elderly incontinence sufferers. For more active wearers whether infants or adults, the bag should preferably be anatomically shaped such that the bag follows the contours of the body and can be worn inconspicuously by the wearer under normal garments. In addition, the bag 14 is preferably shaped to allow at least partial insertion and retention of the bag in-between the buttocks of the wearer and thereby ensure good contact with the flange and the skin of the wearer. The bag 14 is preferably designed to provide sufficient volume for fecal material under a variety of wearing conditions, also when worn by a freely moving, i.e. not bedridden wearer. Sitting on the bag, for example, will result in a largely reduced volume in some areas of the bag. Thus, the bag is preferably shaped to provide sufficient volume in areas which are not subjected to much pressure in wearing conditions such as sitting. The bag 14 is designed to safely contain any entrapped material, typically it will be liquid impermeable, yet it may be breathable. The bag 14 is designed of sufficient strength to withstand rupture in use, also when pressure on the bag 14 is exerted in typical wearing conditions, such as sitting. The bag 14 may be provided from a unitary piece of material or from a number of separate pieces of material, which may be identical or different and which are sealed at their respective peripheries.

The bag typically has a wearer facing surface and a garment facing surface. The wearer facing surface of bag is disposed adjacent the buttocks of the wearer. As such, the wearer facing surface amply covers the buttocks of the wearer and does not hang between the thighs of the wearer. In one preferred embodiment the bag 14 has a wearer facing portion 20 and a garment facing portion 22 which comprise separate pieces of material. The wearer facing portion 20 and the garment facing portion 22 are sealed at the periphery of the bag 14, thus creating a bag peripheral rim 24. In the embodiment shown in FIG. 1, the wearer facing portion 20 comprises a plane-like sheet having the bag aperture 16. The garment facing portion 22 comprises a sheet being three-dimensionally expansible to provide a space between the garment facing surface 22 and the wearer facing surface 20 and to contain the fecal material inside the bag. Alternatively, the garment facing surface may comprise a three-dimensionally expansible sheet. The three-dimensionally expansible sheet may be formed by folding a plane sheet such that the folding is released to expand three-dimensionally when the fecal material is discharged in the bag 14. Alternatively, the three-dimensionally expansible sheet may be formed by a stretchable material such as stretchable film.

The wearer facing portion 22 of the bag 14 may comprise one or multiple layers. Preferably, the wearer facing portion 22 comprises two or more layers including the inner layer 26 and the outer layer 28. The inner layer 26 typically at least partially comes in contact with fecal material. The outer layer 28 typically at least partially comes in contact with the skin of the wearer. The outer layer 28 is preferably a fibrous layer, wherein the fibers are hydrophobic such that said fibers have a wetting time of at least 1 hour, preferably at least 6 hours and most preferably at least 24 hours. The hydrophobicity of the fibrous outer layer is determined according to the liquid absorbency time test as per the ASTM-D 1117-80 method. It has been found that the provision of such a hydrophobic fibrous outer layer provides the bag with particularly pleasing sensation to the skin and in particular when utilized in conjunction with a diaper ensures that fluid is not absorbed by the outer layer of the wall material of the body exudates management device but is absorbed within the core of the diaper. The fibrous outer layer 24 may comprise any fiber which meets the hydrophobicity requirements. Suitable fibers include fibers which meet the hydrophobicity requirements per se such as polyester fibers, polypropylene fibers, polyethylene fibers, polyamide fibers and mixtures thereof. Alternatively fibers which have been treated by the utilization of a particular finishing treatment for example an oil, in order to provide them with the required hydrophobicity requirements may also be effectively utilized herein. Moreover mixtures of hydrophobic fibers or treated hydrophobic fibers may also be utilized. The fibrous outer layer 24 may be provided as a woven or a nonwoven layer, preferably a nonwoven. The inner layer 26 is preferably a liquid impermeable layer to prevent body exudates such as fecal material contained in the bag 14 from leaking.

In one preferred embodiment, the wearer facing portion 22 may comprise a laminate formed from two layers which comprises a nonwoven outer layer 24 and a film inner layer 26. Alternatively, the wearer facing portion 22 may comprise three or more layers, preferably one film and two nonwoven layers. In an even more preferable embodiment the film is interposed between the two nonwoven layers. This sequence of layers results in a closed fibrous structure, which has a particularly pleasing sensation on contact with the skin of the wearer.

Exemplary nonwovens utilized for the outer layer 24 include felt fabrics, spunlaced fabrics, fluid jet entangled fabrics, air-laid fabrics, wet-laid fabrics, dry-laid fabrics, melt-blown fabrics, staple fiber carding fabrics, spunbonded fabrics, stitch-bonded fabrics, apertured fabrics, combinations of the above or the like. Such nonwovens present an uneven surface to the skin of the wearer and thus reduce significantly the problem of occlusion and greatly improves skin healthiness. The nonwoven for the outer layer 24 is preferably a hydrophobic fibrous nonwoven layer. Preferably, the nonwoven is treated with a surface active material, such as a fluorchemical or other hydrophobic finishings, to provide the requisite hydrophobicity. The nonwoven, however, may equally be treated with coatings of liquid impervious materials such as hot-melt adhesives or coatings of silicone or other hydrophobic compounds such as rubbers and vegetable and mineral waxes or it may be physically treated using nano-particulates or plasma coating techniques, for example. The nonwoven can also be treated with agents to improve the tactile perceivable softness of the wearer facing portion 20. The agents include but are not limited to vegetable, animal or synthetic oils, silicone oils and the like. The presence of these agents are known to impart a silky or flannel-like feel to the nonwoven layer without rendering it greasy or oily to the tactile sense of the wearer. Additionally, surfactant material, including anionic, non-anionic, cationic and non-cationic surfactants, may be added to further enhance softness and surface smoothness. Furthermore, the nonwoven layer may be impregnated with a lotion to provide desirable therapeutic or protective coating lotion benefits. The lotion coating on the wearer facing portion 20 is transferable to the skin of the wearer by normal contact and wearer motion and/or body heat. Generally, mineral oil in the form of a lotion is recognized as being effective in imparting a soothing, protective coating to the skin of the wearer. It is also possible to impregnate the nonwoven layer with a solid oil phase of cream formulation or to incorporate into the nonwoven layer an array of pressure- or thermal- or hydrorupturable capsules containing for example, baby oil.

Exemplary films for the inner layer 26 include a thermoplastic material. The thermoplastic material can be selected from among all types of hot-melt adhesives, polyolefins especially polyethylene, polypropylene, amorphous polyolefins, and the like; material containing meltable components comprising fibers or polymeric binders including natural fibers such as cellulose—wood pulp, cotton, jute, hemp; synthetic fibers such as fiberglass, rayon, polyester, polyolefin, acrylic, polyamid, aramid, polytetrafluroethylene metal, polyimide; binders such as bicomponent high melt/low melt polymer, copolymer polyester, polyvinyl chloride, polyvinyl acetate/chloride copolymer, copolymer polyamide, materials comprising blends wherein some of the constituent materials are not meltable; air and vapour permeable materials including microporous films such as those supplied by EXXON Chemical Co., III, US under the designation EXXAIRE or those supplied by Mitsui Toatsu Co., Japan under the designation ESPOIR NO; and monolithic breathable materials such as Hytrel™ available from DuPont and Pebax™ available from ELF Atochem, France. The film for the inner layer 26 is liquid impervious and preferably permeable to gases such as air and to vapour such as water vapour in order to avoid the problem of entrapment and condensation of moisture vapour given off by the body of the wearer and thus, the hot, clammy and uncomfortable conditions after a short period of use.

The garment facing portion 24 of the bag 14 may also comprise one or multiple layers. Preferably, the garment facing portion 24 comprises two or more layers including an inner layer and the outer layer. The inner layer of the garment facing portion at least partially comes in contact with fecal material. The outer layer of the garment facing portion at least partially comes in contact with the wearer's garment or the wearer's absorbent article such as a diaper. The inner layer of the garment facing portion 24 may comprise the same material as that of the inner layer 26 of the wearer facing portion 22. The outer layer of the garment facing portion 24 may comprise the same material as that of the outer layer 28 of the wearer facing portion 22. Alternatively, the inner layer and/or the outer layer of the garment facing portion 24 may comprise materials different from the layers of the wearer facing portion 22.

Absorbent materials may be provided inside the bag 14. The absorbent material may comprise any absorbent material which is capable of absorbing and retaining liquids. The absorbent material may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The absorbent material may be positioned in the bag 14 in any suitable manner. For example, the absorbent material may be loosely arranged within the bag or may be secured to the inner layer of the bag 14. Any known techniques for securing absorbent material to nonwoven and film substrates may be used to secure the absorbent material to the inner layer of the bag. The absorbent material may also be arranged to have any desired shape or configuration (e.g., rectangular, oval, circular, etc.).

The bag aperture 16 is provided on the bag 14 as shown in FIGS. 1 and 2 whereby fecal material is received from the body through the bag aperture 16 prior to storage within the bag cavity. The bag aperture 16 is provided on the wearer facing portion 20 of the bag 14. The bag aperture 16 may be provided in any shape or size, such as circular, oblong, heart shaped and may be symmetrical or asymmetrical, preferably the aperture has an oblong configuration either in the longitudinal or in the transversal direction. The bag aperture may be in the center of the wearer facing portion 20, or may be shifted toward the front end 30 of the wearer facing portion 20 or the back end 32 of the wearer facing portion 20. In the embodiment shown in FIG. 1, the bag aperture 16 has a modified oblong configuration extending in the transverse direction and is shifted toward the front end 30 of the wearer facing portion 20.

The second attachment means 36 is provided for attachment of the bag 14 to the perianal area of the wearer adjacent to, preferably surrounding the bag aperture 16. The second attachment means 36 may be directly provided on the surface of the bag 14 or may be provided on a flange sheet (second flange sheet) 18 which is joined to the surface of the bag 14 if such a second flange sheet is provided. The second attachment means 36 may be formed by one or more materials for the first attachment 50 as described above. Preferably, the first attachment means 50 and the second attachment means 36 are formed by the same material. In the embodiment shown in FIGS. 1 and 2, the first attachment means 50 and the second attachment means 36 are continuously integrally formed by the same material. Alternatively, the first attachment means 50 and the second attachment means 36 are formed by separate and/or different materials. When the first attachment means 50 and the second attachment means 36 are continuously integrally formed, the integrated attachment means comprises two ring-like objects. The connected portion 72 of the integrated attachment means including a portion of the first attachment means 50 an the second attachment means 36 serves as a separator to separate the body fluid management device 12 and the bag 10 such that the feces contained in the bag 10 does not leak toward the genitalia are of the wearer. Therefore, it is preferable that the connected portion 72 has adhesion sufficient to secure the body exudates management device 10 to the wearer's body. However, it is also preferable that the width of the connected portion 72 between the bag aperture 16 and the fluid pervious topsheet 56 is minimized such that the connected portion 72 does not interfere with discharge of urine to the body fluid management device 12 and discharge of fecal material into the bag 10. The connected portion 72 may have a width of between 1 mm and 25 mm, preferably between 3 mm and 15 mm, more preferably between 5 mm and 10 mm. The connected portion 72 is positioned between the anus and the genitalia of the wearer when the device is applies to the wearer's body.

The second attachment means 36 is preferably covered with a release means (not shown) in order to protect the second attachment means 36 such as siliconized paper. Before application of the body exudates management device 10 to the skin of the wearer, the release means if present is removed.

The second flange sheet 18, if provided (in the embodiment shown in FIGS. 1 and 2, it is provided), is joined to the bag 14 according to any means known to the skilled in the art which may provide permanent or releasable attachment. Preferably, the second flange sheet 18 is attached to the bag 14 by adhesive. Preferably, the bag 14 is joined to the second flange sheet 18, towards the outer periphery of second flange sheet 18 so as not to cause any obstruction for the entering fecal material. The second flange sheet 18 may be provided in any size depending on the wearer group for which the device is intended. Similarly the second flange sheet 18 may be provided in any shape. In the embodiment shown in FIGS. 1 and 2, the second flange sheet 18 is generally coextensive with the second attachment means 36, more preferably is a little larger than the second attachment means 36 to support the entirety of the second attachment means 36. The second flange sheet 18 has a plurality of lobes 34 which is non-adhesive and can thereby serve to facilitate placement and removal of the device whilst avoiding contact with the adhesive. The lobes 34 may be provided with a soft material such as a nonwoven thereon. The second flange sheet 18 may be formed by one or more materials for the first flange sheet 68 as described above. Preferably, the first flange sheet 68 and the second flange sheet 18 are formed by the same material. In the embodiment shown in FIGS. 1 and 2, the first flange sheet 68 and the second flange sheet 18 are continuously integrally formed by the same material. Alternatively, the first flange sheet 68 and the second flange sheet 18 are formed by separate and/or different materials.

The body fluid management device 12 is joined to the bag 10 such that the body fluid management device 12 comes in close relation with the bag aperture 16. The position of the body fluid management device 12 is determined with respect to the position of the bag aperture 16 such that the center of the body fluid management device 12 is preferably positioned to come to the genitalia area of the wearer (i.e., the area of urethra and vagina for female and the area of the penis for male) when in use and the bag aperture 16 is positioned to come to the perianal area of the wearer when in use. The body fluid management device 12 and the bag 10 are joined to one another to form the body exudates management device 10 by any known methods to join two objects. In the embodiment shown in FIGS. 1 and 2, the body fluid management device 12 is joined to the bag 10 by adhesive attachment (not shown in FIGS. 1 and 2) between the peripheral edge 66 and the peripheral rim 24 adjacent the front end 30 of the wearer facing portion 20 of the bag 10. Further, the flange sheet integrally and continuously formed from the first flange sheet 68 and the second flange sheet 18 provides another means to join the body fluid management device 12 and the bag 10.

The body exudates management device 10 of the present invention has been found to be particularly useful and beneficial when used in conjunction with absorbent articles such as a disposable diaper 100 as shown in FIG. 3. A preferred diaper 100 shown in FIG. 3 comprises a body portion 102 and a refastenable fastening device 104. A preferred body portion 102 comprises a liquid pervious topsheet 106, a liquid impervious backsheet 110 and an absorbent core (not shown) positioned between the topsheet 106 and the backsheet 110, elastically contractible leg cuffs 112, and a barrier cuff 114 disposed inboard of the leg cuff 112. The body exudates management device 10 is preferably first joined to the body by the first and second attachment means 50 and 36 before the disposable diaper 100 is applied such that the body fluid management device 12 covers the genitalia area of the wearer and the bag 10 covers the perianal area of the wearer. Then, the diaper 100 is positioned over the body exudates management device 10 and fastened in a conventional manner around the body of the wearer. When the body exudates management device 10 is worn with the diaper 100, the opposite surface 54 of the body fluid management device 12 preferably comes in contact with the topsheet 106 of the diaper 100. As a result, discharged fecal material is contained into the bag 10 and discharged urine is acquired by the body fluid management device 12 and then passes through the body fluid management device 12 (more concretely, through the fluid pervious topsheet 56, the acquisition layer 60, the distribution layer 62 and the fluid pervious backsheet 58) toward the topsheet 106 of the diaper 100 whereby the fecal material and urine are separated each other. The discharged urine is then absorbed through the topsheet of the diaper 100 into the absorbent core of the diaper 100. Since fecal material is contained in the bag 10, the fecal material does not contaminate the skin of the wearer other than the skin portion exposed to the bag aperture 16. Further, since the genitalia area is protected by the body fluid management device 12, the genitalia of the wearer is not contaminated by the fecal material leaked out of the bag 10 even if it leaks.

Figure 4:
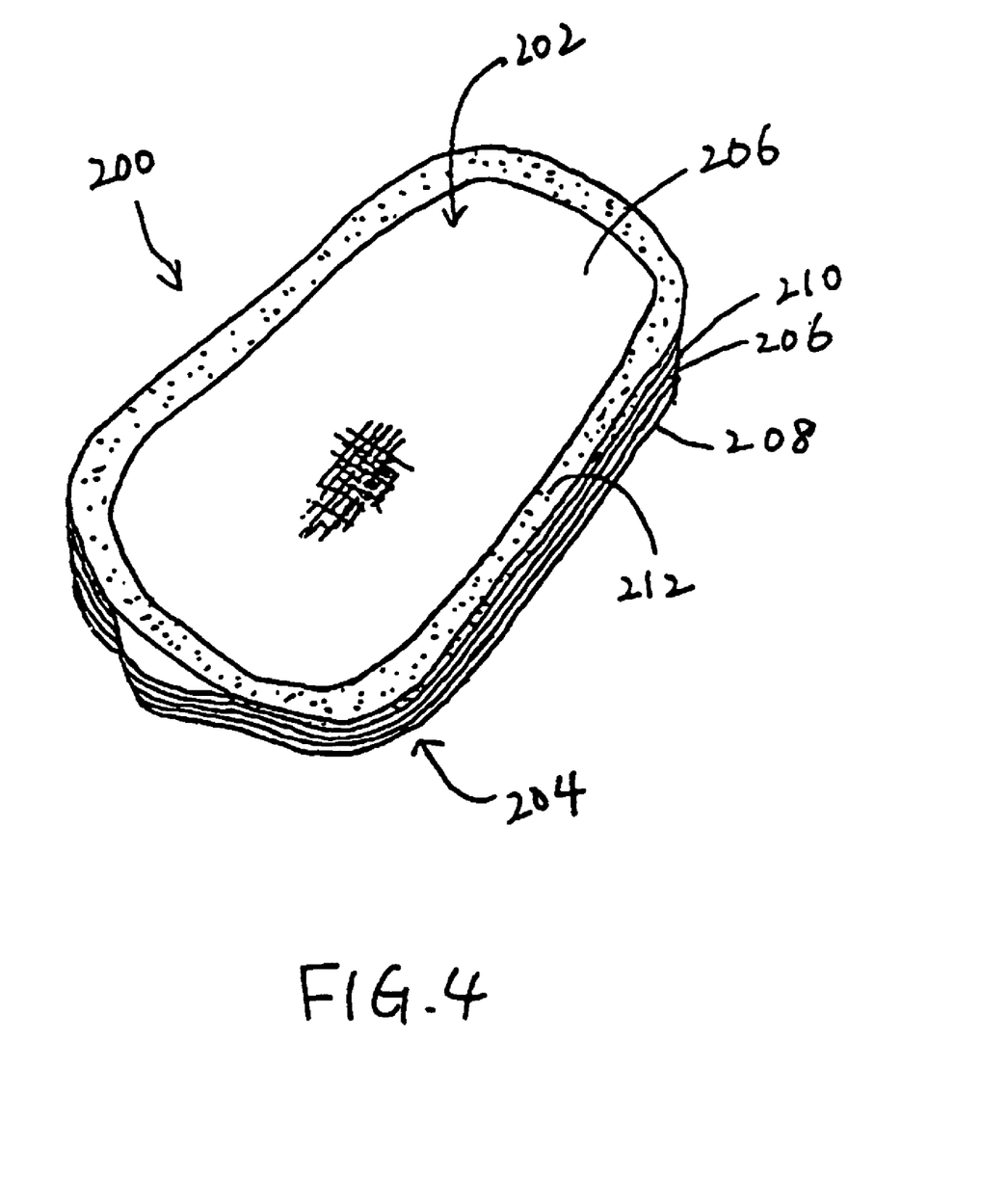
FIG. 4 is a perspective view of an alternative embodiment of a body fluid management device of the present invention.

FIG. 4 shows an another embodiment of the body fluid management device of the present invention. The body fluid management device 200 shown in FIG. 4 has a structure similar to the body fluid management device 12 shown in FIGS. 1 and 2 except for the fact that the body fluid management device 200 is not joined to a bag. The body fluid management device 200 has a body facing surface 202 and an opposite surface 204. The body fluid management device 202 comprises a fluid pervious topsheet 206, a fluid impervious backsheet 208, an acquisition layer and a distribution layer (not shown in FIG. 4). The body fluid management device 200 further comprises a first attachment means 212 for adhesive attachment to the body of the wearer to cover the genitalia area of the wearer. The first flange sheet 210 may be provided between the first attachment means 212 and the periphery of the topsheet 206. The body fluid management device 200 may be used alone or with other articles such as absorbent articles. For example, the body fluid management device 200 may be used with a disposable diaper as shown in FIG. 3. Alternatively, the body fluid management device 200 may be used with female protection devices such as a sanitary napkin. In either case, the body fluid management device 200 is preferably joined to wearer's body by the attachment means to protect the genitalia area of the wearer from body exudates discharged.

It should also be understood that all of the limits and ranges specified herein include all narrower ranges, limits, and amounts that are within the specified limits and ranges and that such narrower ranges and limits may be claimed even though those limits and ranges are not separately listed. While particular embodiments of the present invention have been illustrated and described, it would be obvious to those skilled in the art that various other changes and modifications can be made without departing from the spirit and scope of the invention.

What is claimed is:

1. A body fluid management device used with an absorbent article, the body fluid management device having a body facing surface and an opposite surface facing the absorbent article when used with the absorbent article, wherein the body fluid management device comprises a first attachment means provided on the body facing surface for attachment to the body of the wearer to cover the genitalia area of the wearer and an acquisition layer disposed between the body facing surface and the opposite surface, and at least a portion of the body facing surface is fluid pervious and at least a portion of the opposite surface is fluid pervious such that fluid passes through the body fluid management device from the body facing surface toward the opposite surface.

2. The body fluid management device of claim 1 wherein the body fluid management device comprises a distribution layer disposed underneath the acquisition layer.

3. The body fluid management device of claim 1 wherein the body fluid management device comprises a fluid pervious topsheet disposed on the body facing surface and a fluid pervious backsheet disposed on the opposite surface, and the acquisition layer is disposed between the fluid pervious topsheet and the fluid pervious backsheet.

4. The body fluid management device of claim 3 wherein the first attachment means is provided at the periphery of the body fluid management device.

5. The body fluid management device of claim 4 wherein the fluid pervious backsheet comprises a fluid impervious material having a backsheet aperture therein.

6. A body exudates management device used with an absorbent article, wherein the body exudates management device comprises a body fluid management device and a bag, the body fluid management device has a body facing surface and an opposite surface facing the absorbent article when used with the absorbent article and comprises a first attachment means provided on the body facing surface for attachment to the body of the wearer to cover the genitalia area of the wearer and an acquisition layer disposed between the body facing surface and the opposite surface, wherein at least a portion of the body facing surface is fluid pervious and at least a portion of the opposite surface is fluid pervious such that fluid passes through the body fluid management device from the body facing surface toward the opposite surface, the bag has a bag aperture and a second attachment means for attachment to the perianal area of the wearer, the second attachment means provided adjacent to the bag aperture, and the body fluid management device is joined to the bag.

7. The body exudates management device of claim 6 wherein the body fluid management device is joined to a portion of the bag adjacent to the bag aperture.

8. The body exudates management device of claim 6 wherein the body fluid management device comprises a fluid pervious topsheet disposed on the body facing surface and a fluid pervious backsheet disposed on the opposite surface, and the acquisition layer is disposed between the fluid pervious topsheet and the fluid pervious backsheet.

9. The body exudates management device of claim 8 wherein the first attachment means is provided at the periphery of the body fluid management device.

10. The body exudates management device of claim 9 wherein a portion of the periphery of the body fluid management device is joined to a portion of the bag.

11. The body exudates management device of claim 10 wherein the first attachment means and the second attachment means are provided integrally.

* * * * *